(12) United States Patent
Garrigues et al.

(10) Patent No.: US 8,765,118 B2
(45) Date of Patent: Jul. 1, 2014

(54) *LACTOCOCCUS LACTIS* STRAIN WITH HIGH VITAMIN K2 PRODUCTION

(75) Inventors: Christel Garrigues, Frederiksberg (DK); Martin Bastian Pedersen, Copenhagen (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 13/817,110

(22) PCT Filed: Aug. 11, 2011

(86) PCT No.: PCT/EP2011/063838
§ 371 (c)(1),
(2), (4) Date: Feb. 14, 2013

(87) PCT Pub. No.: WO2012/031851
PCT Pub. Date: Mar. 15, 2012

(65) Prior Publication Data
US 2013/0142765 A1 Jun. 6, 2013

(30) Foreign Application Priority Data
Aug. 17, 2010 (EP) .................................... 10173036

(51) Int. Cl.
*A01N 63/00* (2006.01)
*C12N 1/12* (2006.01)
*C12N 1/20* (2006.01)
*A01N 63/02* (2006.01)
*A61K 35/00* (2006.01)
*A23C 9/12* (2006.01)
*A23L 1/28* (2006.01)

(52) U.S. Cl.
USPC .................... 424/93.4; 435/252.1; 435/252.9; 424/780; 426/34; 426/61

(58) Field of Classification Search
CPC ....... A61K 35/744; A61K 35/74; A61K 8/99; A61K 38/018; A23V 2002/00; A23V 2250/206; A23V 2200/306; A23V 2250/714; A23V 2250/7144; A23V 2200/31; C12N 15/01; C12N 1/04; A23L 1/3014; A23L 1/0345

See application file for complete search history.

(56) References Cited

U.S. PATENT DOCUMENTS

2010/0047385 A1* 2/2010 Garault et al. .................... 426/7
2010/0047396 A1* 2/2010 Garault et al. .................. 426/72

FOREIGN PATENT DOCUMENTS

| WO | WO-2008/040784 A1 | 4/2008 |
| WO | WO-2008/040793 A1 | 4/2008 |
| WO | WO-2009/095240 A1 | 8/2009 |
| WO | WO-2010/139690 A1 | 12/2010 |

OTHER PUBLICATIONS

Aliabadi et al., "Prevalence of Malnutrition in Free Living Elderly People in Iran: a Cross-Sectional Study," Asia Pacific Journal of Clinical Nutrition, 17(2):285-289 (2008).
Beulens et al., "High Dietary Menaquinone Intake is Associated with Reduced Coronary Calcification," Atherosclerosis, 203:489-493 (2009).
Booth et al., "Dietary Intake and Adequacy of Vitamin K," Journal of Nutrition, Recent Advances in Nutritional Sciences, 128: 785-788 (1998).
Brooijmans et al., "Heme and Menaquinone Induced Electron Transport in Lactic Acid Bacteria," Microbial Cell Factories, 8(28) (2009).
Extended European Search Report for European 10173036.4, dated Oct. 15, 2010.
Gast et al., "High Menaquinone Intake Reduces the Incidence of Coronary Heart Disease," Nutrition, Metabolism & Cardiovascular Diseases, 19:504-510 (2009).
Geleijnse et al., "Dietary Intake of Menaquinone Is Associated with a Reduced Risk of Coronary Heart Disease: The Rotterdam Study," American Society for Nutritional Society, Nutritional Epidemiology, 3100-3105 (2004).
International Search Report for Application No. PCT/EP2011/063838, dated Feb. 11, 2011.
Iwamoto et al., "Effects of Vitamin K2 on Osteoporosis," Current Pharmaceutical Design, 10, 2557-2576 (2004).
Iwamoto et al., "High-Dose Vitamin K Supplementation Reduces Fracture Incidence in Postmenopausal Women: A Review of the Literature," Nutrition Research, 29:221-228 (2009).
Kamao et al., "Vitamin K Content of Foods and Dietary Vitamin K Intake in Japanese Young Women," Journal of Nutritional Science and Vitaminology, 53:464-470 (2007).
MacDonald et al., "Vitamin K Intake is Associated with Higher Bone Mineral Density and Reduced Bone Resorption in Early Postmenopausal Scottish Women: No Evidence of Gene-Nutrient Interaction with Apolipoprotien E Polymorphisms," American Journal of Clinical Nutrition, 87:1513-1520 (2008).
Morishita et al., "Production of Menaquinones by Lactic Acid Bacteria," Journal of Dairy Science, 82:1897-1903 (2009).

(Continued)

*Primary Examiner* — Chris R Tate
*Assistant Examiner* — Douglas F White
(74) *Attorney, Agent, or Firm* — Foley & Lardner LLP

(57) ABSTRACT

The present invention relates to a novel wild-type *Lactococcus lactis* subsp. *cremoris* bacteria strain with increased vitamin K2 production and mutants and variants thereof and methods for preparation of a fermented food or feed product enriched in vitamin K2 and a vitamin K enriched edible product for amelioration and/or prevention of vitamin K deficiency. The present invention also relates to the fermented food or feed product and the edible product obtainable by the methods herein and to the wild-type *Lactococcus lactis* subsp. *cremoris* bacteria strain for use in treatment and/or prevention of vitamin K deficiency in a mammal, such as a human.

13 Claims, No Drawings

(56) References Cited

OTHER PUBLICATIONS

Nimptsch et al, "Dietary Intake of Vitamin K and Risk of Prostate Cancer in the Heidelberg Cohort of the European Prospective Investigation into Cancer and Nutrition (EPIC-Heidelberg)," American Journal of Clinical Nutrition, 87:985-992 (2008).

Rees et al., "Is Vitamin K Consumption Associated with Cardio-MetabolicDisorders? A Systematic Review," Maturitas, 121-128 (2010).

Sato et al, "Efficient Production of Menaquinone (Vitamin $K_2$) by a Menadione-Resistant Mutant of *Bacillus subtilis*," Journal of Industrial Microbiology & Biotechnology, 26:115-120 (2001).

Shearer et al., "Chemistry Nutritional Sources, Tissue Distribution and Metabolism of Vitamin K with Special Reference to Bone Health," The Journal of Nutrition, 126:118S-1186S (1996).

Shearer et al., "Metabolism and Cell Biology of Vitamin K," Journal of Thrombosis and Haemostasis, 100:530-547 (2008).

Shurgers et al, "Vitamin K-Containing Dietary Supplements: Comparison of Synthetic Vitamin K and Natto-Derived Menaquinone-7," Blood, 109(8):3279-3283 (2007).

Van Summeren et al., "Vitamin K Status is Associated with Childhood Bone Mineral Content," British Journal of Nutrition, 100, 852-858 (2008).

Vergnaud et al., "Undecarboxylated Osteocalcin Measured with a Specific Immunoassay Predicts Hip Fracture in Elderly Women: The EPIDOS Study," Journal of Clinical Endocrinology and Metabolism, 82(3):719-724 (1997).

Vermer et al., "Beyond Deficiency: Potential Benefits of Increased Intakes of Vitamin K. for Bone and Vascular Health," European Journal of Nutrition, 43:325-335 (2004).

Yokoyama et al., "Vitamin K2 Includes Autophagy and Apoptosis Simultaneously in Leukemia Cells," Autophagy, 4:5, 629-640 (2008).

\* cited by examiner

LACTOCOCCUS LACTIS STRAIN WITH HIGH VITAMIN K2 PRODUCTION

CROSS-REFERENCE TO RELATED APPLICATIONS

This application is a national phase of PCT/EP2011/063838, filed Aug. 11, 2011, which was published on Mar. 15, 2012, as WO 2012/031851, which claims the benefit of EP 10173036.4, filed Aug. 17, 2010. The respective contents of these documents are incorporated here by reference in their entirety.

FIELD OF THE INVENTION

The present invention relates to a novel *Lactococcus lactis* subsp. *cremoris* strain with increased vitamin K2 production and use of this strain for preparing a vitamin K2 enriched fermented food or feed product and an edible product for amelioration and/or prevention of vitamin K deficiency in a mammal (e.g. a human).

BACKGROUND ART

Lactic acid bacteria (LAB) are intensively used in the dairy industry for making different animal milk fermented products, such as e.g. yoghurt or cheese, and have achieved Generally Recognized As Safe (GRAS) status. Studies have shown that some lactic acid bacteria produce vitamin K2. The quantity of vitamin K2 synthesized by these bacteria generally varies from 29 to 90 µg/L for fermented milk (Morishita et al., 1999).

Vitamin K is important for a number of human/animal health issues such as bone health. In nature, vitamin K is present in two forms, K1 (phylloquinone) in green plants, and K2 (menaquinone, MK) in many bacteria. The MK can be further classified depending on the length of the side chain (MK–n, where n denotes the number of isoprenyl side-chain units). The lactic acid bacteria *Lactococcus lactis* and *Leuconostoc lactis* are natural producers of vitamin K2 (Morishita et al., 1999), albeit normally at a low level. The vitamin K2 is a constituent of the bacterial plasma membrane where it shuttles electrons as an essential component of the respiratory chain. A third synthetic vitamin K exists, K3 (menadione).

The major dietary source of vitamin K is K1 from vegetables and oils. The highest concentrations of K1 have been shown for green leafy vegetables—for instance spinach (Kamao et al., 2007). There are also low amounts of K1 in fish and animals. K2 is less widely distributed than K1, but high amounts can be found in livers and fermented foods, such as natto fermented with *Bacillus subtilis* (Sato et al., 2001). Dairy products also contain K2. In a Japanese study, the MK-4 content of cream and cheese were found to be 8 µg/100 g and 5 µg/100 g, respectively (Kamao et al., 2007). In a European study, the MK-8 content in cheese was 5-10 µg/100 g, and the MK-9 content was 10-20 µg/100 g in the same product (Shearer et al., 1996). Note that during cheese production the curd is concentrated about 10-fold thus greatly increasing the concentration of vitamin K2.

K2 has a substantially longer half-life than K1 in the body, and in a human clinical trial, intake of MK-7 had a more beneficial effect on bone health compared to K1 (Schurgers et al., 2007). Vitamin K is present in the blood and can be measured by HPLC-MS.

Vitamin K is an essential co-factor for the formation of γ-carboxyglutamic acid (Gla) residues in proteins. Gla-containing proteins are important for blood coagulation and tissue calcification through binding with calcium.

Osteocalcin (Oc) is a bone matrix protein involved in the mineralization of bone. In this process vitamin K is a co-factor. Oc is dependent on three residues of Gla, and the orientation of the Gla residues helps Oc to bind tightly to calcium ions. Research so far shows that Oc plays an important role in mineralization and remodeling of the bone tissue. Furthermore, several studies have shown that high levels of undercarboxylated osteocalcin (ucOc) is associated with lower bone mineral density and higher risk for bone fracture (Vergnaud et al., 1997).

Human studies have shown that the required daily intake should be at least 1 µg/kg body weight (Booth and Suttie, 1998). This is sufficient for efficient blood clotting but research has indicated that more vitamin K is required for strong bone health. A dose of 45 mg/day e.g. about 500-fold higher of vitamin K was beneficial for postmenopausal woman regarding bone health (Iwamoto et al., 2009). This shows that vitamin K has a wide safety range. It should be noted that vitamin K2 appears to have a higher potential regarding bone health than K1.

Osteoporosis is a metabolic bone disease, characterized by a low bone mass and micro-architectural deterioration of bone tissue, leading to enhanced bone fragility and a consequent increase in fracture risk. Osteoporosis is an increasing problem worldwide, and it has been estimated by World Health Organization (WHO) that in 2050, 6 million hip fractures will occur. This results in enormous loss in quality of life and cost for society.

Treating postmenopausal women with K1 and K2 as a drug for osteoporosis have shown increased bone mineral density and reduced risk of fracture (Macdonald et al., 2008; Vermeer et al., 2004). In elderly, high vitamin K levels in the serum was associated with lower fracture risk (Aliabadi et al., 2008). Thus, addition of K2 in food should be beneficial for bone health. Children would in particular benefit with an increased intake of vitamin K (van Summeren et al., 2008).

In vitro, vitamin K has been shown to have anticancer effects regarding prostate cancer cells, liver and gut tumors and some leukemia cell lines (Nimptsch et al., 2008; Shearer and Newman, 2008; Yokoyama et al., 2008). Dietary intake of K2, but not K1, has been shown to have an inverse association with prostate cancer. Vitamin K2 from dairy products has been shown to be more efficient than vitamin K2 from meat (Nimptsch et al., 2008).

Dietary intake of K2, but not K1, has been shown to reduce the risk of coronary heart disease (CHD) in older men and women (Geleijnse et al., 2004). Furthermore, in another study with 16,000 people, it was shown that MK-7, MK-8, and MK-9 from cheese and curd cheese protected against cardiovascular disease (Gast et al., 2009). Further evaluation of this data-set showed that every increase of 10 µg of K2 (but not K1) decreased the risk of cardiovascular disease by 9% (Beulens et al., 2009).

Generally speaking, the amount of vitamin K2 produced by previously known wild-type LAB is not sufficiently high to make a commercially relevant product comprising vitamin K2—e.g. a dairy product with a sufficiently high amount of vitamin K2.

Accordingly, there is a need for additional lactic acid bacteria which are able to produce increased amounts of vitamin K2—see e.g. WO2008/040793A1—and for food products and medicaments that contain vitamin K2 in sufficiently high quantities to contribute to satisfying requirements and, if necessary correcting deficiencies. Furthermore, an intrinsically produced source of vitamin K2, such as that produced by for example *Lactococcus lactis* is to be preferred over vitamin K added as a purified compound, as this has a more "natural appeal" and will result in a more simplified product label, i.e. a "clean label".

Further, in WO2008/040784A1 it is described that an increased amount of produced vitamin K2 can be obtained by fermenting milk with LAB under conditions, where the LAB are not in the growth phase but in what is termed "resting cells" phase in WO2008/040784A1 (see e.g. claim 1). Essentially, this is obtained by adding a relatively large amount of LAB to the milk. It was found herein that cells grown under respiration conditions (presence of heme under agitation) have a significantly increased vitamin K2 production.

Previously, we have shown that strains having an inactivated thyA gene, encoding thymidylate synthase, produce highly increased amounts of vitamin K2 (WO2010/139690A1). Although this mutant produces increased amounts of vitamin K2 it requires specialized conditions to be propagated. It would thus be more convenient with a wild-type strain that can be produced using standard production methods.

SUMMARY OF THE INVENTION

It is an object of the present invention to provide a wild-type lactic acid bacterium (LAB) which is capable of producing a significantly increased amount of vitamin K2 under standard fermentation conditions and to provide cost-efficient and accessible methods for preparing vitamin K enriched fermented food or feed products as well as for preparing other edible products, such as food products and medicaments, for treatment and/or prevention of vitamin K deficiency.

Additional objects will become apparent hereinafter and still others will be obvious to one skilled in the art to which the invention pertains.

The inventors have proceeded with extensive screening and research in order to achieve the above-described objectives and solved the objects based on the identification of a new wild-type *Lactococcus lactis* subsp. *cremoris* strain CHCC12464, which is capable of producing a high amount of vitamin K2. The wild-type strain is both relatively simple to handle and to utilize for production of high amounts of biomass.

Another advantage of this wild-type strain is that it may be possible to use this as a starting point to further optimize the production of vitamin K2.

Accordingly, a first aspect of the invention relates to the novel, wild-type *Lactococcus lactis* subsp. *cremoris* strain CHCC12464 that was deposited with the Deutsche Sammlung von Mikroorganismen and Zellkulturen under accession No. DSM 23588, and mutants and variants thereof, with high vitamin K2 production.

A second aspect of the invention relates to a method for preparing a fermented food or feed product enriched in vitamin K2 comprising:
a) inoculating a suitable substrate with *Lactococcus lactis* subsp. *cremoris* strain CHCC12464 with accession No. DSM 23588 or a mutant or variant thereof;
b) fermenting the substrate under favorable conditions, such as standard fermentation conditions, for vitamin K2 production and/or for the metabolism of the bacteria;
c) optionally adding further microorganisms and/or additives to the substrate; and
d) optionally packaging the fermented food or feed product.

In a third aspect the invention concerns a fermented food or feed product enriched in vitamin K2 obtainable by the implementation of a method according to the second aspect of the invention.

In a fourth aspect, the invention relates to a fermented food or feed product comprising *Lactococcus lactis* subsp. *cremoris* strain CHCC12464 with accession No. DSM 23588, and mutants and variants thereof.

In a fifth aspect of the invention is provided a non-therapeutic method for increasing the strength of the bones of a subject, comprising the step of administering to the subject a fermented food or feed product according to the third or fourth aspect of the invention.

A sixth aspect of the invention relates to a vitamin K2-enriched lactic ferment comprising *Lactococcus lactis* subsp. *cremoris* strain CHCC12464, and mutants and variants thereof, obtainable by fermenting *Lactococcus lactis* subsp. *cremoris* strain CHCC12464, and mutants and variants thereof, under favorable conditions, such as standard fermentation conditions.

In a seventh aspect the present invention relates to a method for production of vitamin K2 comprising:
a) culturing *Lactococcus lactis* subsp. *cremoris* strain CHCC12464, or a mutant or variant thereof, under conditions favorable for the metabolism of the bacteria and/or for vitamin K2 production; and
b) recovering the vitamin K2 produced.

In an eight aspect the invention concerns a method for preparing an edible product, notably a food or a feed product or a medicament enriched in vitamin K2 for treating and/or preventing vitamin K deficiency in a mammal.

According to one embodiment one such method comprises:
a) adding the lactic ferment according to the sixth aspect of the present invention and/or vitamin K2 produced by the method according to the seventh aspect of the invention and/or *Lactococcus lactis* subsp. *cremoris* strain CHCC12464, or a mutant or variant thereof, to the edible product, to a starting material of same, or to an intermediate preparation of same; and
b) obtaining the edible product enriched in vitamin K2.

In a ninth aspect the invention concerns an edible product enriched in vitamin K2 obtainable by the implementation of a method according to the seventh aspect of the invention.

In a tenth aspect the invention relates to an edible product comprising *Lactococcus lactis* subsp. *cremoris* strain CHCC12464 with accession No. DSM 23588, and mutants and variants thereof.

In an eleventh aspect the present invention relates to an edible product according to the ninth or tenth aspect for use as a medicament.

In a twelfth aspect the invention concerns an edible product according to the ninth, tenth or eleventh aspect for use in treating and/or preventing a disease selected from the group consisting of vitamin K deficiency, osteoporosis, cancer, such as prostate cancer, and cardiovascular diseases, such as coronary heart diseases, in a mammal.

In a thirteenth aspect the present invention relates to *Lactococcus lactis* subsp. cremoris strain CHCC12464 for use as a medicament.

In a fourteenth aspect the present invention concerns *Lactococcus lactis* subsp. cremoris strain CHCC12464 for use in treating and/or preventing a disease selected from the group consisting of vitamin K deficiency, osteoporosis, cancer, such as prostate cancer, and cardiovascular diseases, such as coronary heart diseases, in a mammal.

The present invention in further aspects relates to the use of *Lactococcus lactis* subsp. cremoris strain CHCC12464, and mutants and variants thereof, for the preparation of a food product for treating and/or preventing vitamin K deficiency, osteoporosis, cancer, such as prostate cancer, and cardiovascular diseases, such as coronary heart diseases in a mammal as well as the use of *Lactococcus lactis* subsp. *cremoris* strain CHCC12464, and mutants and variants thereof, for the preparation of a medicament for treating and/or preventing of vitamin K deficiency, osteoporosis, cancer, such as prostate cancer, and cardiovascular diseases, such as coronary heart diseases in a mammal.

Furthermore, the invention relates to *Lactococcus lactis* subsp. *cremoris* strain CHCC12464, and mutants and variants thereof, for use in treating and/or preventing vitamin K deficiency. More specifically, the invention relates to *Lactococcus lactis* subsp. *cremoris* strain CHCC12464, and mutants and variants thereof, for use in treating and/or preventing of vitamin K deficiency, osteoporosis; cancer, such as prostate cancer; and cardiovascular diseases, such as coronary heart diseases.

Furthermore, use of an edible product comprising the *Lactococcus lactis* subsp. cremoris strain CHCC12464 that was deposited with the Deutsche Sammlung von Mikroorganismen and Zellkulturen under accession No. DSM 23588 or a strain which has been derived therefrom, for treating and/or preventing a disease selected from the group consisting of vitamin K deficiency, osteoporosis, cancer, such as prostate cancer, and cardiovascular diseases, such as coronary heart diseases, in a mammal.

DETAILED DESCRIPTION OF THE INVENTION

Definitions

In the present context, the term "milk" comprises milk of a mammal or a plant. Examples of milk are cow's milk (bovine milk), camel milk, buffalo milk, goat's milk, sheep's milk, and soy milk. Optionally the milk is acidified, e.g. by addition of an acid (such as citric, acetic, or lactic acid), or mixed, e.g. with water. The milk may be raw or processed, e.g. by filtering, sterilizing, pasteurizing, homogenizing etc., or it may be reconstituted dried milk. An important example of "bovine milk" according to the present invention is pasteurized cow's milk. It is understood that the milk may be acidified, mixed, or processed before, during, and/or after the inoculation with bacteria.

The term "fermented milk product" refers to products which are intended for animal, more specifically human, consumption and which are derived from acidifying lactic fermentation by a lactic acid bacterium of a milk substrate. Such products may contain secondary ingredients, such as fruits, vegetables, sugars, flavors, etc.

The term "fermented food or feed product" refers to products which are intended for human or animal consumption, respectively, and which are derived from acidifying lactic fermentation by a lactic acid bacterium of a suitable substrate, such as, for example milk, fruit juices, wine, beer, and soy sauce. Such products may contain secondary ingredients such as fruits, vegetables, sugars, flavors, etc.

By "fermentation" is meant a biochemical reaction which involves releasing energy from an organic substrate by the action of microorganisms. In particular "lactic fermentation" is an anaerobic or microaerobic process of the consumption of among other lactose by the bacteria in the ferments, which causes the formation of lactic acid, and potentially acetic acid, and a lowering of the pH. The term "respiration" herein refers to a biochemical reaction which involves releasing energy from an organic substrate in the presence of oxygen and a heme source. In particular, several lactoccocal strains have been shown to thrive and undergo respiration when grown under respiratory conditions.

In the present context, a fermented milk "starter culture" is a bacterial culture which comprises at least one strain of lactic acid bacteria, e.g. *Lactococcus lactis, Lactobacillus bulgaricus* or *Streptococcus thermophilus*. In accordance herewith, a fermented milk product is obtainable by inoculating milk and fermenting the milk with the strains added.

In the present context, the term "packaging" (a suitable amount of) the fermented food or feed product in a suitable package relates to the final packaging of the fermented food or feed product to obtain a product that can be ingested by or administered to a subject, such as a human or an animal, or a group of subjects. A suitable package may thus be a bottle, a carton, or similar, and a suitable amount may be e.g. 10 mL to 5000 mL or 50 mL to 1000 mL.

The term "bacteria" in the present context is in plural since it makes no sense to here talk about compositions comprising only one single bacterium.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pediococcus* spp., and *Enterococcus* spp., and the order "Actinomycetales" which includes *Brevibacterium* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria.

The terms "isolated bacteria" or "isolated *Lactococcus lactis* subsp. *cremoris* strain CHCC12464" should be understood as bacteria or *Lactococcus lactis* subsp. *cremoris* strain CHCC12464 bacteria, respectively, isolated after a suitable fermentation in a suitable medium—e.g. milk or a well known bacteria growth medium such a M17 medium. The skilled person is able to ferment and isolate/harvest the bacteria by techniques which are well known in the field, e.g. isolation/harvesting by centrifugation.

In the present context, the term "mutant" should be understood as a strain derived from a strain of the invention (or used in the invention) by means of e.g. genetic engineering, radiation, UV light, chemical treatment, and/or other methods that induce changes in the genome. It is preferred that the mutant is a functionally equivalent mutant. A preferred mutant of a strain of the invention is a mutant that has high vitamin K production, e.g. a mutant that has substantially the same, or improved, vitamin K producing properties as the mother strain. Such a mutant is a part of the present invention. Especially, the term "mutant" refers to a strain obtained by subjecting a strain (such is a strain of the invention) to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments are carried out. In a presently preferred mutant, less than 1%, or less than 0.5%, or less than 0.1%, or even less than 0.01% of the nucleotides in the bacterial genome have been changed to another nucleotide, deleted, or an additional nucleotide inserted, compared to the mother strain. The mutant may also be a spontaneous mutant.

It is clear for the skilled person that by using the deposited strain as starting material, the skilled reader can by conventional mutagenesis or re-isolation techniques routinely obtain further mutants or derivatives therefrom that retain the herein described relevant features and advantages. Accordingly, the term "a strain which has been derived therefrom" relates to mutant strains obtained by using the deposited strain as starting material.

In the present context, the term "variant" should be understood as a strain which is functionally equivalent to a strain of the invention, e.g. having substantially the same, or improved, properties (e.g. regarding viscosity, gel stiffness, mouth coating, flavor, and/or post acidification). Such variants, which may be identified using appropriate screening techniques, are a part of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Implementation and Aspects of the Invention

The inventors of the present invention found in a screening of several lactic acid bacteria strains, specifically of the species *Lactococcus lactis*, that the *Lactococcocus lactis* subsp. *cremoris* strain CHCC12464 was superior in vitamin K2 production and produced up to 22 μg/100 mL, or 220 μg/L, of vitamin K2 (see Example 1). Thus, the present invention provides a biologically pure culture of a strain of lactic acid bacteria, which have been selected for its ability to produce high amounts of vitamin K2.

A sample of the inventive, new *Lactococcus lactis* subsp. *cremoris* strain CHCC12464 was deposited pursuant to, and in satisfaction of, the requirements of the Budapest Treaty on the International Recognition of the Deposit of Microorganisms for the Purposes of Patent Procedure with Deutsche Sammlung von Mikroorganismen and Zellkulturen (DSNIZ) GmbH, Inhoffenstr. 7B, D-38124 Braunschweig, Germany in 2010 under the accession No. DSM 23588.

*Lactococcus lactis* subsp. *cremoris* strain CHCC12464 is particularly suitable for preparation of fermented food and feed products by inoculation of a suitable substrate and fermentation under favorable conditions, such as standard fermentation conditions for *Lactococcus* bacteria readily known to the skilled person, to obtain a lactic ferment comprising *Lactococcus lactis* subsp. *cremoris* strain CHCC12464.

Accordingly, in one aspect the present invention relates to a method for preparing a fermented food or feed product enriched in vitamin K2, comprising:
  a) inoculating a suitable substrate with *Lactococcus lactis* subsp. *cremoris* strain CHCC12464, or a mutant or variant thereof;
  b) fermenting the substrate under conditions favorable for metabolism and/or vitamin K2 production of *Lactococcus lactis* subsp. *cremoris* strain CHCC12464.
  c) optionally adding further microorganisms and/or additives to the substrate; and
  d) optionally packaging the fermented food or feed product.

In a preferred embodiment the fermented food or feed product is a fermented milk product in which case the suitable substrate is milk.

As is known to the skilled person various fermented milk products can be obtained by fermentation of milk with different lactic acid bacteria. In a preferred embodiment the fermented milk product is a product selected from the group consisting of yoghurt, drinking yoghurt, stirred yoghurt, set yoghurt and a yoghurt-like drink, bitter milk, butter milk, sour cream, fresh cheese and cheese.

Generally speaking, the skilled person knows suitable fermenting conditions to ferment milk with the herein relevant bacteria. Herein suitable conditions include, but is not limited to, where the milk is inoculated with the bacteria and fermented at around 30° C. for *Lactococcus lactis* (but normally about 10° C. higher for "yoghurt cultures" with *Streptococcus thermophilus* and *Lactobacillus bulgaricus*) until reaching a pH of 4.4 to 4.6 (roughly after around 8 hours). Cooling the milk to +6° C. slows the fermentation and growth of *Lactococcus lactis* subsp. *cremoris* strain CHCC12464. The standard fermentation conditions may be modified if necessary by the person skilled in the art, on the basis of general knowledge and, possibly after routine experimentation.

It may be advantageous to add a relatively large amount of LAB to the milk in order to obtain higher vitamin K production.

In a preferred embodiment the *Lactococcus lactis* subsp. *cremoris* strain CHCC12464 is inoculated with from $1 \times 10^6$ to $1 \times 10^{10}$ CFU (colony forming units) of bacteria per ml of milk substrate.

Measuring the viable cell count is done by quantifying the number of colony forming units (CFU) of *Lactococcus lactis* subsp. *cremoris* strain CHCC12464 in serial dilutions by colony counting on agar plates, according to standard methods in the art. Suitable medium and incubation conditions are known to the skilled person and as given in Example 1 below.

If desired, one may add extra bacteria (e.g. extra *Lactococcus lactis* subsp. *cremoris* strain CHCC12464) at some point of interest (e.g. after completion of the fermentation).

The milk may in step a) be inoculated with at least one other strain of lactic acid bacteria. It should be understood that the milk may be inoculated separately/sequentially with each bacterial species, or simultaneously with two or more bacterial species. It is presently preferred that the milk is inoculated with all bacterial species at the same time. This is conveniently done by inoculating the milk with a starter culture comprising the bacterial species.

According to a preferred embodiment the at least one strain of bacteria is one or more bacteria of the genus *Lactococcus, Streptococcus, Lactobacillus, Leuconostoc, Pseudoleuconostoc, Pediococcus, Brevibacterium, Enterococcus, Propionibacterium* and *Bifidobacterium*.

According to an embodiment of the present invention, the fermented milk product is conveniently packaged in a sealed package that contains from 10-5000 ml of the product, such as from 25 to 3000 ml or from 50 to 1000 ml. Exemplary packages may contain 10-300 ml, 20-200 ml or 30-100 ml.

Fermented milk products comprising *Lactococcus lactis* subsp. *cremoris* strain CHCC12464 as described herein can also be used as an additive to e.g. be put into other edible food products, such as curd cheeses, chocolates, juices, meat products and dried milk powder products for young infants (infant formulas).

In a further aspect, the invention relates to a fermented food or feed product enriched in vitamin K2 and obtainable by the above-described method.

In an additional aspect, the invention relates to a fermented food or feed product comprising *Lactococcus lactis* subsp. *cremoris* strain CHCC12464 with accession No. DSM 23588, and mutants and variants thereof.

The skilled person can by use of well known assays (see e.g. Morishita et al. 1999) routinely determine the amount of vitamin K2 in the fermented food or feed product as such (e.g. a fermented milk or a yoghurt).

Further, the skilled person can easily determine the amount of herein described *Lactococcus lactis* subsp. *cremoris* strain CHCC12464 in the fermented food or feed product.

Finally, the skilled person can routinely determine the average amount of vitamin K2 present on average in the individual bacteria of the food or feed product and thereby routinely identify how much of the vitamin K2 that is derived from the presence of the CHCC12464 bacteria in the edible product.

Such a fermented food or feed product may be termed a functional food or feed product, thanks to the high vitamin K content and the use of it for treatment and/or prevention of vitamin K deficiency.

A functional food or feed product as described herein may have instructions (e.g. in the form of a label or a leaflet) informing the consumer of the high vitamin K content of the product (e.g. a fermented milk, a yoghurt or a cheese).

A further aspect of the invention relates to a method for increasing the strength of the bones of a subject, such as a human, livestock, or a pet animal, the method comprising the step of administering to the subject the fermented food or feed product enriched in vitamin K2.

The present invention in another aspect relates to a vitamin K2 enriched lactic ferment obtainable by fermenting *Lactococcus lactis* subsp. *cremoris* strain CHCC12464 bacteria under standard fermentation conditions well-known to the skilled person and described herein. The standard fermentation conditions may be modified if necessary by the person skilled in the art, on the basis of general knowledge and, possibly after routine experimentation. The culture medium is an appropriate medium for culturing *Lactococcus* spp. strains.

The lactic ferment may be in liquid form, dry form, spray-dried, frozen or in the form of a lyophilisate. According to a preferred embodiment the lactic ferment is dried. According to another preferred embodiment the lactic ferment is in the form of at least one lyophilisate.

According to an aspect of the present invention vitamin K2 may be produced by a method comprising:
  a) culturing *Lactococcus lactis* subsp. *cremoris* strain CHCC12464, or a mutant or variant thereof, under conditions favorable for vitamin K2 production; and
  b) recovering the vitamin K2 thus produced.

Vitamin K2 obtained by the above-mentioned method and/or *Lactococcus lactis* subsp. cremoris strain CHCC12464, or a mutant or variant thereof, and/or a lactic ferment comprising this strain may be used as a component in a method for producing an edible product, such as a food product or a medicament, enriched in vitamin K2.

According to a further aspect of the present invention the method for preparing an edible product enriched in vitamin K2 comprises addition of *Lactococcus lactis* subsp. cremoris strain CHCC12464, or a mutant or variant thereof, and/or vitamin K2 produced by the above-mentioned method and/or a lactic ferment comprising
*Lactococcus lactis* subsp. *cremoris* strain CHCC12464 in the edible product, in a starting material of same, or in an intermediate preparation of same and obtaining the finished edible product enriched in vitamin K2.

Another aspect of the present invention relates to an edible product obtainable by such a method.

Yet another aspect of the present invention relates to an edible product comprising *Lactococcus lactis* subsp. *cremoris* strain CHCC12464 with accession No. DSM 23588, and mutants and variants thereof.

*Lactococcus lactis* subsp. *cremoris* strain CHCC12464, or a mutant or variant thereof, and/or the lactic ferment can be implemented by using pre-cultured and isolated bacteria. The bacteria may be in fresh or frozen state. Alternatively, and in a preferred embodiment, the bacteria are dried. Preferably the bacteria are in the form of at least one lyophilisate.

The bacteria are, in all cases, added to the edible product, to a starting material of same, or to the intermediate preparation of same in a completely conventional manner.

Such an edible product enriched in vitamin K2 may be useful for increasing vitamin K levels in a mammal, such as a human, livestock, or a pet animal. The edible product may in a preferred embodiment be a food product and in another preferred embodiment be a medicament.

A herein commercially relevant edible product obtainable by the method of the present invention is e.g. a fermented milk food product (such as a dairy food product), such as a yoghurt or a cheese.

Accordingly, in a preferred embodiment the edible product is a food or feed product—preferably a food product.

Preferably, the food product is animal milk fermented with *Lactococcus lactis* subsp. cremoris strain CHCC12464, or a mutant or variant thereof, as described herein—e.g. preferably a dairy product.

Preferably, the dairy product is at least one dairy product selected from the list consisting of: milk, yoghurt and cheese.

Preferably, the animal milk is cow milk or goat milk.

Such a food product may be termed a functional food product, thanks to the high vitamin K content and the use of it for treatment and/or prevention of vitamin K deficiency.

A functional food product as described herein may have instructions (e.g. in the form of a label or a leaflet) informing the consumer of the high vitamin K content of the product (e.g. a fermented milk, a yoghurt or a cheese), and in the case of a pharmaceutical preparation possibly also dosages.

As already discussed above, in another preferred embodiment the edible product is a medicament. The medicament may be in the form of capsules, tablets, or powder.

As discussed above, the vitamin K2 is a constituent of the bacterial plasma membrane—i.e. vitamin K2 is present in the membrane of the LAB.

In a preferred embodiment the edible product comprises isolated *Lactococcus lactis* subsp. *cremoris* strain CHCC12464 bacteria—preferably dried or freeze-dried, isolated *Lactococcus lactis* subsp. *cremoris* strain CHCC12464, or a mutant or variant thereof.

If the edible product is solid the amount of vitamin K2 may be measured as µg/mg by methods known to the skilled person. An example of such a product could for example comprise a dried composition of isolated *Lactococcus lactis* subsp. *cremoris* strain CHCC12464, or a mutant or variant thereof, as such—such dried composition could e.g. be put into a pharmaceutically relevant capsule and then e.g. sold as a medicament.

The edible product and/or the lactic ferment according to the present invention may further comprise other bacteria (e.g. thyA(−) mutant bacteria, or other types of lactic acid bacteria, such as, for example, *Lactobacillus bulgaricus* and *Streptococcus thermophilus* bacteria) in addition to the *Lactococcus lactis* subsp. *cremoris* strain CHCC12464 strain.

The present invention also relates to use of *Lactococcus lactis* subsp. *cremoris* strain CHCC12464, or a mutant or variant thereof, for the preparation of a food product for treating and/or preventing vitamin K deficiency as well as to use of *Lactococcus lactis* subsp. *cremoris* strain CHCC12464, or a mutant or variant thereof, for the preparation of a medicament for treating and/or preventing vitamin K deficiency.

As known to the skilled person, the term "vitamin K deficiency" is a well known and defined pathological condition for the skilled person.

Below some common general knowledge in relation to vitamin K deficiency is described.

Vitamin K deficiency is a form of avitaminosis resulting from insufficient vitamin K. Vitamin K-deficiency may occur by disturbed intestinal uptake (such as would occur in a bile duct obstruction), by therapeutic or accidental intake of vitamin K-antagonists or, very rarely, by nutritional vitamin K deficiency. As a result, Gla-residues are inadequately formed and the Gla-proteins are insufficiently active.

Lack of control of the three processes mentioned above may lead to the four following: stomach pains; risk of massive uncontrolled bleeding; cartilage calcification; and severe malformation of developing bone or deposition of insoluble calcium salts in the walls of arteries. The deposition of calcium in soft tissues, including arterial walls, is quite common, especially in those suffering from atherosclerosis, suggesting that Vitamin K deficiency is more common than previously thought.

As discussed above vitamin K deficiency is well known to be associated with decreased bone health—e.g. malformation of developing bone or bone strength.

Accordingly, in a preferred embodiment the treatment and/or prevention of vitamin K deficiency is for improving bone health in a mammal. The improvement of bone health may be related to less malformation of developing bone.

In preferred embodiments the treatment and/or prevention of vitamin K deficiency are for treatment and/or prevention of osteoporosis; cancer, such as prostate cancer; cardiovascular diseases, such as coronary heart diseases.

Alternatively, the treatment and/or prevention of vitamin K deficiency are for treatment and/or prevention of stomach pains; risk of uncontrolled bleeding or cartilage calcification.

Whether it is treatment or prevention of vitamin K deficiency will generally depend on the type of composition used (e.g. dairy product or a medicament).

Certain aspects of the present invention relates to use of *Lactococcus lactis* subsp. cremoris strain CHCC12464, or a mutant or variant thereof, for the preparation of a food product and a medicament, respectively, for treating and/or preventing vitamin K deficiency in a mammal.

According to the present invention further aspects relates to:

*Lactococcus lactis* subsp. *cremoris* strain CHCC12464 with accession No. DSM 23588, or a mutant or variant thereof, for use in treating and/or preventing vitamin K deficiency in a mammal.

*Lactococcus lactis* subsp. *cremoris* strain CHCC12464 with accession No. DSM 23588, or a mutant or variant thereof, for use in treating and/or preventing osteoporosis in a mammal.

*Lactococcus lactis* subsp. *cremoris* strain CHCC12464 with accession No. DSM 23588, or a mutant or variant thereof, for use in improvement of bone health in a mammal.

*Lactococcus lactis* subsp. *cremoris* strain CHCC12464 with accession No. DSM 23588, or a mutant or variant thereof, for use in reduction of malformation of developing bone in a mammal.

*Lactococcus lactis* subsp. *cremoris* strain CHCC12464 with accession No. DSM 23588, or a mutant or variant thereof, for use in treating and/or preventing stomach pains in a mammal.

*Lactococcus lactis* subsp. *cremoris* strain CHCC12464 with accession No. DSM 23588, or a mutant or variant thereof, for use in treating and/or preventing cancer in a mammal.

*Lactococcus lactis* subsp. *cremoris* strain CHCC12464 with accession No. DSM 23588, or a mutant or variant thereof, for use in treating and/or preventing prostate cancer in a mammal.

*Lactococcus lactis* subsp. *cremoris* strain CHCC12464 with accession No. DSM 23588, or a mutant or variant thereof, for use in treating and/or preventing cardiovascular diseases in a mammal.

*Lactococcus lactis* subsp. *cremoris* strain CHCC12464 with accession No. DSM 23588, or a mutant or variant thereof, for use in treating and/or preventing coronary heart diseases in a mammal.

In case it is a dairy product (e.g. a yoghurt)—the e.g. yoghurt may be sold to "healthy" people and it may therefore be seen as prevention of vitamin K deficiency (e.g. "normal" people obtain an improvement of their general bone health and therefore there is a prevention of bone problems).

In the case that the composition is a medicament, it may be more related to treatment of evidently sick people—e.g. a person with severe malformation of developing bone or a person with stomach pains.

In short, in the present context the skilled person will easily be able to identify the difference between treatment and prevention of vitamin K deficiency.

Commercially, the herein most relevant mammal is a human. Alternatively, the mammal may e.g. be a cow, a pig, a goat, a dog, a cat or a rabbit.

The skilled person may—based on common knowledge—identify how much composition should preferably be administered to the mammal. If the composition is e.g. yoghurt it will of course essentially be up to the consumer how much yoghurt he/she wants to eat. If the composition is e.g. a medicament, the physician will know how much the patient should have to get the treatment/prevention.

Embodiments of the present invention are described below, by way of non-limiting examples.

EXAMPLES

Example 1

Vitamin K2 is an essential component of the respiratory chain in the cell membrane of *Lactococcus lactis* and other microorganisms where it shuttles electrons. Cells thus need vitamin K2 to be able to respire. We therefore speculated that cells growing to a high yield under respiratory production conditions may produce high amounts of vitamin K2.

We therefore tested a large array of wild-type lactic acid bacteria strains of the species *Lactococcus lactis* for vitamin K2 production using an internal assay (data not shown). Briefly, the assay was as follows: cells from a respiratory stationary culture were inoculated at OD600=1.0 into 7.5 mL of fresh 3.5% fat milk and incubated for ca. 20 hrs (see below for details). After fermentation the fat in the fermented milk was degraded by lipase and the proteins were precipitated. Hereafter the menaquinone (MK) was liberated by sonication and extraction by hexane:chloroform. The amount of MK in the sample was determined by HPLC-MS. The column used was a LiChroCart 125-2, Superspher 100 RP-18 equipped with a 0.45 Dm in-line filter. The mobile phase was a gradient of 2-propanol and methanol. The assay was calibrated using MK-4 and MK-7 standards.

The most promising strains were thereafter tested externally as described immediately below.

The growth conditions were: 100 mL, M17 (Difco™ M17)+1% lactose, 5 ppm hemin, with agitation at 30° C. An amount of cells to yield an OD600 of 1.0 in a volume of 100 mL was removed and the cells were concentrated by centrifugation at 4° C. The cells were resuspended in 5 mL of "sødmaelk" with 3.5% fat ("full fat" milk from Arla Foods Amba, Viby, Denmark). These 5 mL were inoculated into 95 mL"sødmaelk" at 4° C. thus giving an inoculation level of OD=1.0. After ca. 20 hrs of incubation at 30° C. the sample was frozen at −20° C. and sent to Aquanal (151 bis, Avenue Jean Jaurès, 33600 Pessac, France) on dry-ice for analysis of vitamin K2. The following levels of vitamin K2 were obtained (µg/100 mL milk):

CHCC4079 (5);
CHCC1899 (2);
CHCC3143 (2);
CHCC2862 (9);
CHCC12464 (22);
CHCC12675 (26).

We thus surprisingly identified two wild-type strains CHCC12464 and CHCC12675 which produced 22 µg vitamin K2/100 mL milk and 26 µg vitamin K2/100 mL milk, respectively. The strains are thus 2.5-fold and 3-fold, respectively, better than any other wild-type LABs we know of in respect to vitamin K2 production.

CHCC12464 and CHCC12675 are therefore valuable strains in themselves and may furthermore be excellent starting points for further improvements in vitamin K2 production.

Deposits and Expert Solution

The applicant requests that a sample of the deposited microorganisms stated below may only be made available to an expert, until the date on which the patent is granted.

The *Lactococcus lactis* subsp. *cremoris* strain CHCC12464 was deposited 2010-05-06 at Deutsche Sammlung von Mikroorganismen and Zellkulturen GmbH, Inhoffenstr. 7B, D-38124 Braunschweig (DSMZ) and given the accession number: DSM 23588.

The deposit was made according to the Budapest treaty on the international recognition of the deposit of microorganisms for the purposes of patent procedure.

REFERENCES

Morishita T et al. (1999). J. Dairy. Sci. 82:1897-1903.
Kamao M et al. (2007). Journal of Nutritional Science and Vitaminology 53: 464-470.
Sato T et al. (2001). J. of Industrial Microbiology and Biotechnology 26: 115-120.
Shearer M J et al. (1996). J. Nutr. 126: 1181S-1186.
Schurgers L J et al. (2007). Blood 109: 3279-3283.
Vergnaud P et al. (1997). J. Clin. Endocrin. Metabol. 82: 719-724.
Booth S L and Suttie J W (1998). J. Nutr. 128: 785-788.
Iwamoto J et al. (2009). Nutrition Research (New York, N.Y.) 29: 221-228.
Macdonald H M et al. (2008). The American J. of Clinical Nutrition 87: 1513-1520.
Vermeer C et al. (2004). European Journal of Nutrition 43: 325-335.
Aliabadi M et al. (2008). Asia Pacific Journal of Clinical Nutrition 17: 285-289.
van Summeren M J H et al. (2008). British Journal of Nutrition 100: 852-858.
Nimptsch K et al. (2008). Am J Clin Nutr 87: 985-992.
Shearer M J and Newman P (2008). Thrombosis And Haemostasis 100: 530-547.
Yokoyama T et al. (2008). Autophagy 4: 629-640.
Geleijnse J M et al. (2004). J Nutr 134: 3100-3105.
Gast et al. (2009), Nutrition, Metabolism and Cardiovascular Disease 19: 504-510.
Beulens J W J et al. (2009). Atherosclerosis 203: 489-493.
WO 2008/040793A1
WO 2008/040784A1
WO 2010/139690A1

The invention claimed is:

1. An isolated lactic acid bacteria strain, wherein the lactic acid bacteria strain is *Lactococcus lactis* subsp. *cremoris* strain CHCC12464, which was deposited with the Deutsche Sammlung von Mikroorganismen und Zellkulturen under accession No. DSM 23588 or (ii) a strain derived therefrom having all identifying characteristics of CHCC12464.

2. A method for preparing a fermented food or feed product comprising:
    a) inoculating a suitable substrate with an effective amount of isolated *Lactococcus lactis* subsp. *cremoris* strain CHCC12464 which that was deposited with the Deutsche Sammlung von Mikroorganismen und Zellkulturen under accession No. DSM 23588, or a strain derived therefrom having all identifying characteristics of CHCC12464;
    b) fermenting the substrate under favorable conditions;
    c) optionally adding further microorganisms and/or additives to the substrate; and
    d) optionally packaging the fermented food or feed product.

3. The method according to claim 2, wherein the fermented food or feed product is a fermented milk product and the suitable substrate is milk.

4. The method according to claim 3, wherein the milk is inoculated with from $1\times10^6$ to $1\times10^{10}$ CFU/ml of *Lactococcus lactis* subsp. *cremoris* strain CHCC12464 or the strain which has been derived therefrom having all identifying characteristics of CHCC12464.

5. A fermented food or feed product comprising *Lactococcus lactis* ssubsp. *cremoris* strain CHCC12464 which was deposited with the Deutsche Sammlung von Mikroorganismen und Zellkulturen under accession No. DSM 23588 or a strain derived therefrom having all identifying characteristics of CHCC12464.

6. A method of increasing the strength of the bones of a subject, wherein the method comprises the step of administering to the subject an effective amount of the fermented food or feed product according to claim 5.

7. An isolated lactic ferment comprising *Lactococcus lactis* subsp. *cremoris* strain CHCC12464 which was deposited with the Deutsche Sammlung von Mikroorganismen und Zellkulturen under accession No. DSM 23588 or a strain derived therefrom having all identifying characteristics of CHCC12464.

8. A method for production of vitamin K2 comprising:
   a) culturing an effective amount of isolated *Lactococcus lactis* subsp. *cremoris* strain CHCC12464 which was deposited with the Deutsche Sammlung von Mikroorganismen und Zellkulturen under accession No. DSM 23588 or a strain derived therefrom having all identifying characteristics of CHCC12464, under favorable conditions; and
   b) recovering the vitamin K2 produced.

9. A method for preparing an edible product, comprising adding to the edible product, to a starting material of same, or to an intermediate preparation of same an effective amount of the lactic ferment according to claim 7 and/or isolated *Lactococcus lactis* subsp. *cremoris* strain CHCC12464 which was deposited with the Deutsche Sammlung von Mikroorganismen und Zellkulturen under accession No. DSM 23588 or a strain derived therefrom having all identifying characteristics of CHCC12464.

10. An edible product comprising isolated *Lactococcus lactis* subsp. *cremoris* sstrain CHCC 12464 which that was deposited with the Deutsche Sammlung von Mikroorganismen and Zellkulturen under accession No. DSM 23588 or a strain derived therefrom having all identifying characteristics of CHCC12464.

11. The edible product according to claim 10, wherein the edible product comprises dried isolated *Lactococcus lactis* subsp. *cremoris* strain CHCC12464 with accession No. DSM 23588 or a strain derived therefrom having all identifying characteristics of CHCC12464.

12. A method for treating a mammal having a disease selected from the group consisting of vitamin K deficiency, osteoporosis, cancer, and a cardiovascular diseases, comprising administering to the mammal an effective amount of the edible product according to claim 9.

13. A method for treating a mammal having a disease selected from the group consisting of vitamin K deficiency, osteoporosis, cancer, and a cardiovascular disease, comprising administering to the mammal an effective amount of *Lactococcus lactis* subsp. *cremoris* strain CHCC12464, which was deposited with the Deutsche Sammlung von Mikroorganismen and Zellkulturen under accession No. DSM 23588, or a strain derived therefrom having all identifying characteristics of CHCC12464.

* * * * *